US009580447B2

(12) United States Patent
Maekawa et al.

(10) Patent No.: US 9,580,447 B2
(45) Date of Patent: Feb. 28, 2017

(54) HIGHLY HEAT-RESISTANT PHTHALOCYANINE

(75) Inventors: Masaki Maekawa, Izumi (JP); Daisuke Honda, Izumi (JP); Masakazu Enomura, Izumi (JP)

(73) Assignee: M. TECHNIQUE CO., LTD., Izumi-Shi, Osaka (JP)

(*) Notice: Subject to any disclaimer, the term of this patent is extended or adjusted under 35 U.S.C. 154(b) by 0 days.

(21) Appl. No.: 13/989,082

(22) PCT Filed: Nov. 22, 2011

(86) PCT No.: PCT/JP2011/076967
§ 371 (c)(1),
(2), (4) Date: May 23, 2013

(87) PCT Pub. No.: WO2012/070594
PCT Pub. Date: May 31, 2012

(65) Prior Publication Data
US 2013/0274462 A1    Oct. 17, 2013

(30) Foreign Application Priority Data

Nov. 24, 2010  (JP) .................................. 2010-261863
May 20, 2011   (WO) .................. PCT/JP2011/061692

(51) Int. Cl.
| | |
|---|---|
| C07D 487/22 | (2006.01) |
| C07F 3/06 | (2006.01) |
| B01D 11/02 | (2006.01) |
| B01F 3/08 | (2006.01) |
| C09B 67/14 | (2006.01) |
| C09B 67/22 | (2006.01) |
| C09C 1/00 | (2006.01) |
| C09C 1/62 | (2006.01) |
| C09C 1/04 | (2006.01) |
| C07F 1/08 | (2006.01) |
| B82Y 30/00 | (2011.01) |
| C09B 67/42 | (2006.01) |
| C09B 67/16 | (2006.01) |
| C09B 67/50 | (2006.01) |

(52) U.S. Cl.
CPC ............ *C07F 3/06* (2013.01); *B01D 11/0269* (2013.01); *B01F 3/0861* (2013.01); *B82Y 30/00* (2013.01); *C07F 1/08* (2013.01); *C09B 67/0017* (2013.01); *C09B 67/0019* (2013.01); *C09B 67/0026* (2013.01); *C09B 67/0035* (2013.01); *C09B 67/0092* (2013.01); *C09C 1/0081* (2013.01); *C09C 1/04* (2013.01); *C09C 1/627* (2013.01); *C01P 2004/64* (2013.01); *C01P 2004/82* (2013.01)

(58) Field of Classification Search
CPC .................................................. C07D 487/22
See application file for complete search history.

(56) References Cited

U.S. PATENT DOCUMENTS

| | | | |
|---|---|---|---|
| 6,368,399 | B1 | 4/2002 | Aoba et al. |
| 6,485,658 | B1 | 11/2002 | Horiuchi et al. |
| 2010/0291359 | A1 | 11/2010 | Nogami et al. |
| 2010/0326321 | A1 | 12/2010 | Enomura |
| 2011/0177337 | A1 | 7/2011 | Enomura |
| 2013/0071664 | A1 | 3/2013 | Maekawa et al. |

FOREIGN PATENT DOCUMENTS

| | | |
|---|---|---|
| EP | 0849726 A1 | 6/1998 |
| EP | 2180021 A1 | 4/2010 |
| EP | 2351796 A1 | 8/2011 |
| EP | 2578645 A1 | 4/2013 |
| JP | 5-72773 A | 3/1993 |
| JP | 7-330496 A | 12/1995 |
| JP | 2000-313819 A | 11/2000 |
| JP | 2001-89682 A | 4/2001 |
| JP | 2005-275052 A | 10/2005 |
| JP | 2007-284590 A | 11/2007 |

(Continued)

OTHER PUBLICATIONS

Database WPI Week 200572 Thompson Scientific, London, GB, Oct. 6, 2005, XP-002738769 (2 pages).

*Primary Examiner* — Brian McDowell
(74) *Attorney, Agent, or Firm* — Birch, Stewart, Kolasch & Birch, LLP

(57) ABSTRACT

The problem addressed by the present invention is to provide a high heat-resistant phthalocyanine. The phthalocyanine is separated by mixing a phthalocyanine separation solvent and a phthalocyanine solution wherein a phthalocyanine starting material is dissolved in a solvent. The phthalocyanine is wherein having high heat resistance, the decomposition temperature of the separated phthalocyanine being at least 10° C. higher than the decomposition temperature of the phthalocyanine starting material. Also, the phthalocyanine solution may be the result of dissolving at least two types of phthalocyanine starting material in the solvent, the separated phthalocyanine being wherein containing a solid solvent of the at least two types of phthalocyanine starting material and by the decomposition temperature of the separated phthalocyanine being at least 10° C. higher than the decomposition temperature of a mixture of at least two types of phthalocyanine separated by mixing the phthalocyanine separation solvent and each of at least two types of phthalocyanine solution resulting from dissolving each of the at least two types of phthalocyanine starting material in a solvent.

16 Claims, 9 Drawing Sheets

(56) References Cited

FOREIGN PATENT DOCUMENTS

| | | | |
|---|---|---|---|
| JP | 2008-239870 | A | 10/2008 |
| JP | 2009-132911 | A | 6/2009 |
| JP | 2009-173801 | A | 8/2009 |
| JP | 2009-258415 | A | 11/2009 |
| JP | 4461304 | B1 | 5/2010 |
| JP | 2010-189527 | A | 9/2010 |
| JP | 2011-57772 | A | 3/2011 |
| JP | 2011-138095 | A | 7/2011 |
| WO | WO 2010/035861 | A1 | 4/2010 |
| WO | WO 2010/061830 | A1 | 6/2010 |
| WO | WO 2010/140519 | A1 | 12/2010 |

(A)

13
1
R (B)

1
13
16
d20
n

HIGHLY HEAT-RESISTANT PHTHALOCYANINE

TECHNICAL FIELD

The present invention relates to a highly heat-resistant phthalocyanine.

BACKGROUND ART

A pigment, which is used in a paint, an ink jet ink, a color filter, and so forth, is a color material having better durability than a dye in light resistance, weather resistance, heat resistance, water resistance, and so on. However, especially with regard to heat resistance, for example, a pigment used in a color filter becomes coarse or aggregates in a certain instance during the time of heat treatment at high temperature of 200° C. or higher; and thus, existing pigments have not yet fulfilled the requirements from industries.

Accordingly, proposals have been made with regard to a method such as a method in which pigment's heat resistance is improved by coating around the said pigment particles with a metal compound in a gel form as shown in Patent Document 1 and a method in which a pigment is used as a mixture with a chloride compound as shown in Patent Document 2; however, a pigment having its heat resistance improved without containing a compound other than the said pigment is wanted.

A phthalocyanine pigment widely used in industries has the same problems as mentioned above. Moreover, a phthalocyanine is a material used not only as a color material such as a pigment but also as a charge generating material like an organic photoconductor (OPC), a semiconductor, a catalyst, a solar cell, and so forth; and thus, a phthalocyanine having its heat resistance improved are eagerly wanted.

PRIOR ART DOCUMENTS

Patent Document

Patent Document 1: Japanese Patent Laid-Open Publication No. 2011-57772
Patent Document 2: Japanese Patent Laid-Open Publication No. 2011-138095
Patent Document 3: Japanese Patent No. 4461304

DISCLOSURE OF INVENTION

Problems to be Solved by the Invention

In view of the situation as mentioned above, the present invention provides a highly heat resistant phthalocyanine.

Means for Solving the Problems

An invention according to claim 1 of the present invention relates to a highly heat resistant phthalocyanine, wherein the said phthalocyanine is the phthalocyanine which is separated by mixing a phtalocyanine solution having a phthalocyanine raw material dissolved in a solvent with a phthalocyanine separating solvent, and a decomposition temperature of the separated phthalocyanine is higher by 10° C. or more than a decomposition temperature of the phthalocyanine raw material.

An invention according to claim 2 of the present invention relates to the highly heat resistant phthalocyanine according to claim 1, wherein the separated phthalocyanine contains a copper phthalocyanine having its decomposition temperature of 440° C. or higher.

An invention according to claim 3 of the present invention relates to the highly heat resistant phthalocyanine according to claim 1, wherein the separated phthalocyanine contains a brominated chlorinated zinc phthalocyanine having its decomposition temperature of 515° C. or higher.

An invention according to claim 4 of the present invention relates to the highly heat resistant phthalocyanine according to claim 1, wherein the phthalocyanine solution is a solution having two or more phthalocyanine raw materials dissolved in a solvent, the separated phthalocyanine contains a solid solution of the said two or more phthalocyanine raw materials, and a decomposition temperature of the separated phthalocyanine is higher by 10° C. or more than a decomposition temperature of a mixture of two or more phthalocyanines that are separated by mixing each of two or more phthalocyanine solutions having the two or more phthalocyanine raw materials dissolved into each solvent with a phthalocyanine separating solvent.

An invention according to claim 5 of the present invention relates to the highly heat resistant phthalocyanine according to claim 1, wherein a decomposition temperature of the separated phthalocyanine is 530° C. or higher, and the separated phthalocyanine contains a solid solution of a copper phthalocyanine and a brominated chlorinated zinc phthalocyanine.

An invention according to claim 6 of the present invention relates to the highly heat resistant phthalocyanine according to any one of claims 1 to 5, wherein its decomposition temperature is calculated by simultaneous measurements of thermogravimetry and differential thermal thereof.

An invention according to claim 7 of the present invention relates to the highly heat resistant phthalocyanine according to any one of claims 1 to 6, wherein its decomposition temperature is calculated by simultaneous measurements of thermogravimetry and differential thermal thereof, and the measurements thereof are done under an atmospheric condition with the temperature rising rate of 5° C. per one minute while using the reference sample of α-alumina and the sample weight of 10 mg±0.5 mg.

An invention according to claim 8 of the present invention relates to the highly heat resistant phthalocyanine according to any one of claims 1 to 7, wherein the decomposition temperature thereof is the temperature TR which is the intersection point R between the tangent line L1 at the weight-decrease starting temperature P1 and the tangent line L2 at the weight-decrease ending temperature P2 in the TG curve obtained by simultaneous measurements of thermogravimetry and differential thermal thereof.

An invention according to claim 9 of the present invention relates to the highly heat resistant phthalocyanine according to claim 8, wherein its weight decreasing ratio from 40° C. to the weight-decrease starting temperature P1 in simultaneous measurements of thermogravimetry and differential thermal thereof is 3% or less, and the separated phthalocyanine contains a brominated chlorinated zinc phthalocyanine or a solid solution comprising a copper phthalocyanine and a brominated chlorinated zinc phthalocyanine.

An invention according to claim 10 of the present invention relates to the highly heat resistant phthalocyanine according to any one of claims 1 to 9, wherein the separated phthalocyanine is composed of the particles having particle diameter of 100 nm or less.

If a pigment is crushed into fine particles, especially if a pigment is crushed by using a crushing method, heat resistance of the pigment particles is considered be deteriorated; but the highly heat resistant phthalocyanine according to the present invention is not only composed of the particles having particle diameter of 100 nm or less but also provided with high heat resistance.

An invention according to claim 11 of the present invention relates to the highly heat resistant phthalocyanine according to any one of claims 1 to 10, wherein the phthalocyanine is obtained by separating phthalocyanine microparticles by mixing the phthalocyanine solution with the phthalocyanine separating solvent in a thin film fluid formed between at least two processing surfaces which are disposed in a position they are faced with each other so as to be able to approach to and separate from each other, at least one of which rotates relative to the other.

Form of the pigment particles obtained by crushing by using a crushing method is angular; on the other hand, in the highly heat resistant phthalocyanine according to the present invention, not only the form thereof is nearly spherical but also it is provided with high heat resistance.

An invention according to claim 12 of the present invention relates to the highly heat resistant phthalocyanine according to claim 4, wherein the phthalocyanine is obtained by separating phthalocyanine microparticles by mixing the phthalocyanine solution with the phthalocyanine separating solvent in a thin film fluid formed between at least two processing surfaces which are disposed in a position they are faced with each other so as to be able to approach to and separate from each other, at least one of which rotates relative to the other, and a solid solution ratio of two or more phthalocyanines in a primary particle of the separated phthalocyanine microparticles relative to a ratio of two or more phthalocyanine raw materials in the phthalocyanine solution mixed with the phthalocyanine separating solvent is within 25% as a degree of precision.

Advantages

According to the present invention, a highly heat resistant phthalocyanine than ever could be provided.

This shows a molecular structure of a phthalocyanine without a metal.

FIG. 5

This shows results of the simultaneous measurements of thermogravimetry and differential thermal (TG/DTA measurements) of the highly heat resistant phthalocyanine microparticles obtained in Example 5.

FIG. 6

No. 1 to No. 5 show TEM pictures of the highly heat resistant phthalocyanine microparticles obtained in each of Examples 1 to 5.

FIG. 7

This shows measurement results of particle size distribution of the highly heat resistant phthalocyanine microparticles obtained in each of Examples 1 to 5.

FIG. 8

This shows the STEM-EDS analysis results of the highly heat resistant phthalocyanine microparticles obtained in Example 3, wherein (a) and (b) show the high resolution TEM pictures (HRTEM pictures) of the phthalocyanine microparticles; (c) shows the mapping picture of bromine (Br); (d) shows the mapping picture of copper (Cu); and (e) shows the mapping picture of zinc (Zn).

FIG. 9

This shows results of the simultaneous measurements of thermogravimetry and differential thermal (TG/DTA measurements) of the phthalocyanine microparticles obtained in Example 1 and of the phthalocyanine raw material of Example 1, which is Comparative Example 1.

BEST MODES FOR CARRYING OUT THE INVENTION

Modes for Carrying Out the Invention
Phthalocyanine: Kinds and Crystal Types

Figure 4:
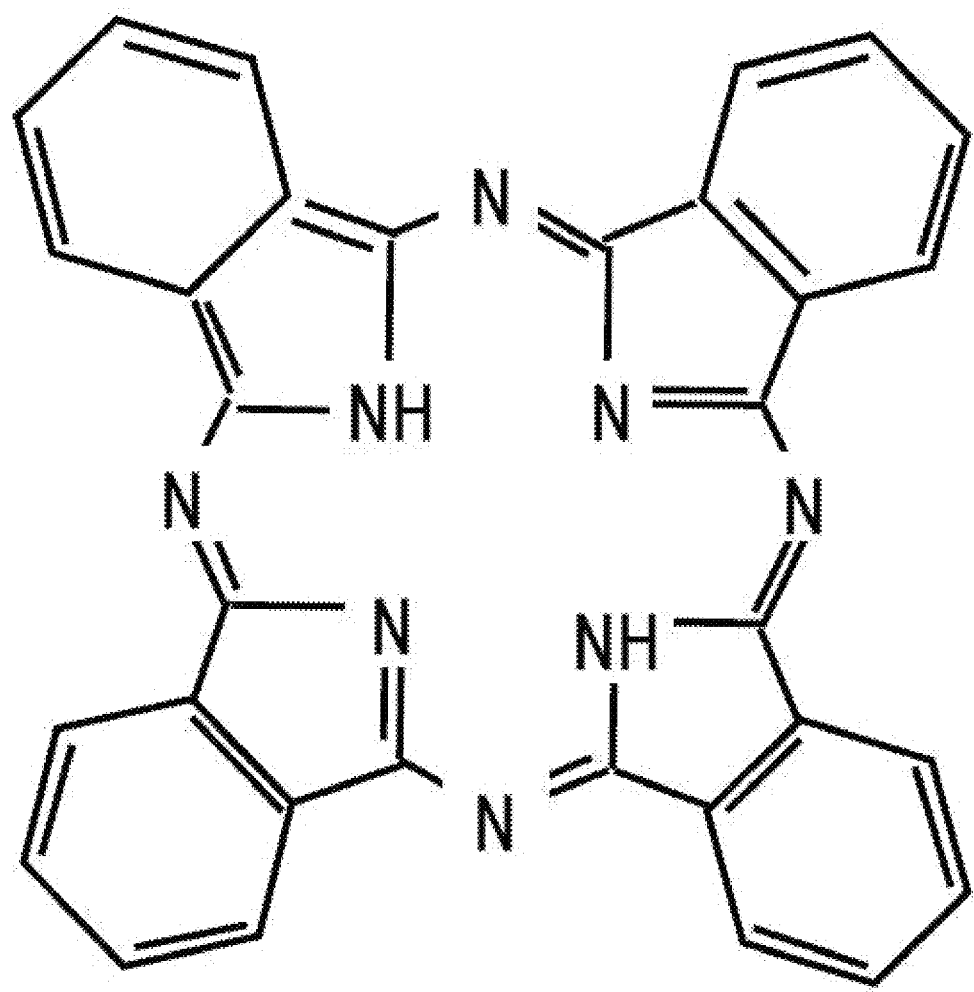
FIG. 4

The phthalocyanine raw material in the present invention is not particularly restricted in its kind. A molecular structure of the phthalocyanine without a metal is shown in FIG. 4 as the phthalocyanine representative. In addition, a phthalocyanine pigment having a structure that two hydrogen atoms in the center of the molecular structure thereof shown in FIG. 4 are substituted with other elements or an atomic group (singular or plural, and single kind or plural kinds) in the periodic table may be used. The element or the atomic group in the center is not particularly restricted. Illustrative example thereof includes H, Cu, Zn, Ti, TiO, Co, Li, Be, Na, Ma, Al, Si, K, Ca, Sc, V, Cr, Mn, Fe, Ni, Ga, Ge, As, Y, Zr, Nb, Mo, Tc, Ru, Ro, Pd, Os, Ir, Pt, Ag, Cd, In, Sn, Sb, Ba, La, Hf, Ta, W, Re, Au, Hg, Tl, Pb, Ac, Th, Pa, and Np. In addition, a phthalocyanine derivative having a part of the molecular structure thereof substituted with other functional groups may be used; or otherwise, a newly synthesized phthalocyanine may be used as well. Further, each of the above-mentioned phthalocyanine raw materials may be used singly or as a mixture of two or more of them. Crystal type of the phthalocyanine is not particularly restricted. In addition, a mixture of plural crystal types thereof may be used as well.

Definition of the High Heat Resistance 1:

The highly heat resistant phthalocyanine according to the present invention is the phthalocyanine that is separated by mixing a phthalocyanine solution having a phthalocyanine raw material dissolved in a solvent with a phthalocyanine separating solvent, wherein a decomposition temperature of the separated phthalocyanine is higher by 10° C. or more than a decomposition temperature of the phthalocyanine raw material.

For example, in the case that the phthalocyanine raw material is a copper phthalocyanine, the decomposition temperature of the separated phthalocyanine is higher than the decomposition temperature of the copper phthalocyanine, and thus, preferably 440° C. or higher, or more preferably 450° C. or higher. In the case that the phthalocyanine raw material is a brominated chlorinated zinc copper phthalocyanine, the decomposition temperature of the separated phthalocyanine is higher than the decomposition temperature of the brominated chlorinated zinc phthalocyanine, and thus, preferably 515° C. or higher, or more preferably 525° C. or higher.

In addition, the highly heat resistant phthalocyanine according to the present invention may be the phthalocyanine that is separated by mixing a phthalocyanine solution having two or more phthalocyanine raw materials dissolved into a solvent with a phthalocyanine separating solvent.

The characteristic feature thereof resides in that the decomposition temperature of the separated phthalocyanine is higher by 10° C. or more than the decomposition temperature of a mixture of two or more phthalocyanines that are separated by mixing each of two or more phthalocyanine solutions having two or more phthalocyanine raw materials dissolved into each solvent with a phthalocyanine separating solvent. The mixing ratio of the mixture of two or more phthalocyanines is assumed to be a dissolution ratio (mol ratio) of two or more phthalocyanine raw materials in the phthalocyanine solution.

In addition, of the highly heat resistant phthalocyanines according to the present invention, the phthalocyanine that is separated by mixing the phthalocyanine solution having two or more phthalocyanine raw materials dissolved into a solvent with the phthalocyanine separating solvent forms a solid solution of two or more phthalocyanine raw materials. An analysis method with regard to the solid solution state of the phthalocyanine is not particularly restricted, though the microscopic analysis is preferable. Especially, an analysis method with which distribution state of the elements in a small area and the weight ratio or the mol ratio thereof can be analyzed is preferable. Illustrative example thereof includes an energy dispersive X-ray spectrometry under observation with a transmission electron microscope (TEM-EDS), an energy dispersive X-ray spectrometry under observation with a scanning electron microscope (SEM-EDS), a high resolution TEM (HRTEM), a high-angle annular dark-field scanning transmission electron microscopy (HAADF-STEM), an element mapping method by using a scanning transmission electron microscope (STEM), and an energy dispersive X-ray spectrometry under observation with a scanning transmission electron microscope (STEM-EDS).

Figure 5:
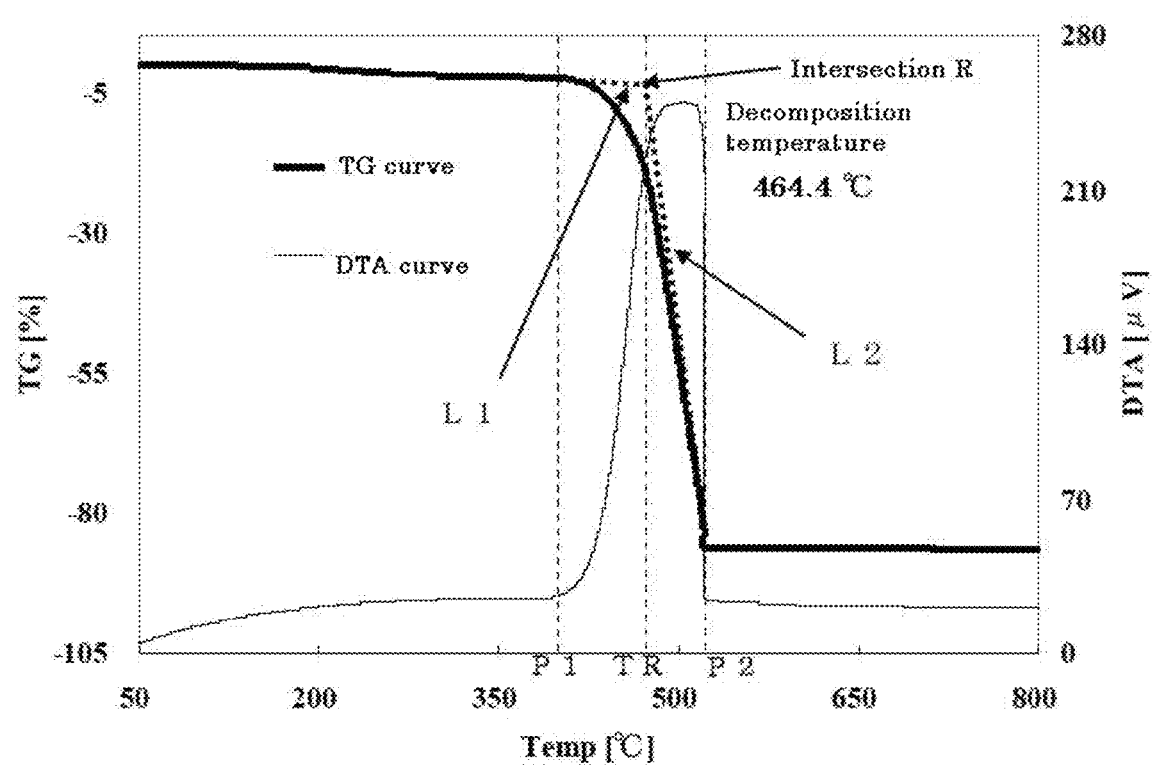

Definition of the High Heat Resistance 2: Measurement Method of TG/DTA and Definition of the Decomposition Temperature The decomposition temperature of the highly heat resistant phthalocyanine according to the present invention is defined as follows. In FIG. 5, results of the simultaneous measurements of thermogravimetry and differential thermal (hereinafter, this is called TG/DTA measurements) of the highly heat resistant phthalocyanine according to the present invention (Example 5) are shown. The decomposition temperature of the highly heat resistant phthalocyanine according to the present invention is the temperature TR which is the intersection point R between the tangent line L1 at P1 and the tangent line L2 at P2 in the TG curve, wherein P1 is the weight-decrease starting temperature and P2 the weight-decrease ending temperature, which are obtained in the TG curve shown in FIG. 5 (in FIG. 5, this point is at 464.4° C.) Alternatively, P1 and P2 may be obtained from the differential curve (DTG curve) of the TG curve. In the present invention, the above-mentioned TG/DTA measurements are done preferably with TG/DTA-6300 (manufactured by Seiko Instruments Inc.), wherein the measurements thereof are done preferably under an atmospheric condition with the temperature rising rate of 5° C. per one minute while using the reference sample of α-alumina and the sample weight of 10 mg±0.5 mg.

Weight Decreasing Ratio from 40° C. To the Decomposition Temperature:

The highly heat resistant phthalocyanine according to the present invention is wherein the weight decreasing ratio thereof from 40° C. to the weight-decrease starting temperature P1 in the above-mentioned TG/DTA measurements is smaller than the weight decreasing ratio of the phthalocyanine raw material from 40° C. to the weight-decrease starting temperature P1 in the above-mentioned TG/DTA measurements. Of the highly heat resistant phthalocyanines according to the present invention, the phthalocyanine that is separated by mixing the phthalocyanine solution having two or more phthalocyanine raw materials dissolved therein with the phthalocyanine separating solvent is wherein the weight decreasing ratio thereof from 40° C. to the weight-decrease starting temperature P1 in the above-mentioned TG/DTA measurements is smaller than the weight decreasing ratio from 40° C. to the weight-decrease starting temperature P1 in the above-mentioned TG/DTA measurements of the mixture of two or more phthalocyanines that are separated by mixing each of two or more phthalocyanine solutions having the two or more phthalocyanine raw materials dissolved into each solvent with the phthalocyanine separating solvent. In this case, the mixing ratio of the mixture of two or more phthalocyanines is assumed to be a dissolution ratio (mol ratio) of two or more phthalocyanine raw materials in the phthalocyanine solution.

Especially in the brominated chlorinated zinc phthalocyanine or the phthalocyanine which is a solid solution comprising the brominated chlorinated zinc phthalocyanine and a phthalocyanine other than this, it is supposed that the weight decreasing thereof from 40° C. to the weight-decrease starting temperature P1 in the above-mentioned TG/DTA measurements is caused by elimination of chlorine or bromine. If these phthalocyanines are used in a color filter, chlorine and bromine that are eliminated during the time of a high temperature treatment may cause problems of corroding a color filter, a display device arranged with it, or wiring therein. Accordingly, in the phthalocyanine such as those of the present invention whose weight decreasing ratio from 40° C. to the weight-decrease starting temperature P1 is small, there is a chance of solving or avoiding the above-mentioned problems.

Particle Diameter:

Particle diameter of the highly heat resistant phthalocyanine according to the present invention is not particularly restricted. In a finely crushed pigment, especially in a pigment that is crushed by using a crushing method, it is considered that heat resistance of the pigment particle is deteriorated. Illustrative example of this crushing method includes crushing methods using a bead mill, a jet mill, and a roll mill. However, in the present invention, the phthalocyanine is phthalocyanine microparticles having their primary particle diameter of 100 nm or less, preferably 50 nm or less, or still more preferably 25 nm or less, and in addition, it is a highly heat resistant phthalocyanine whose decomposition temperature is higher than the decomposition temperature of the phthalocyanine that is used as the raw material thereof, namely, the phthalocyanine raw material.

Of the highly heat resistant phthalocyanines according to the present invention, in the phthalocyanine that is separated by mixing the phthalocyanine solution having two or more phthalocyanine raw materials into a solvent with the phthalocyanine separating solvent, a solid solution ratio of two or more phthalocyanines in a primary particle of the separated phthalocyanine relative to a ratio of two or more phthalocyanine raw materials in the phthalocyanine solution mixed with the phthalocyanine separating solvent is within 25%, preferably within 10%, or more preferably within 5%, as a degree of precision. If the degree of precision is outside of 25%, not only color tone of each phthalocyanine may be different, but also there is a possibility to give adverse effects to its interaction with a solvent or with a dispersing agent, or dispersibility thereof, because of its chemical properties.

A method to obtain the degree of precision in the solid solution ratio of two or more phthalocyanines in a primary particle of the separated phthalocyanine relative to a ratio of two or more phthalocyanine raw materials in the phhtalocyanine solution mixed with the phthalocyanine separating solvent is not particularly restricted provided that the solid solution ratio (component ratio, concentration ratio, or mol ratio) of different phthalocyanines in the primary particle thereof can be obtained; but a preferable method thereof is to use an energy dispersive X-ray spectrometry under observation with a transmission electron microscope (TEM-EDS) with an observation condition of magnification of 250,000 or more, preferably 500,000 or more, or more preferably 1,000,000 or more. In one example thereof, the degree of precision can be obtained from the solid solution ratio (component ratio, concentration ratio, or mol ratio) calculated by the EDS measurement of preferably a primary particle confirmed by the TEM observation with magnification of 250,000 or more relative to the ratio (mol ratio) of two or more phthalocyanine raw materials in the phthalocyanine solution mixed with the phthalocyanine separating solvent. In addition, though not restricted, a STEM-EDS analysis method, a solid NMR method, and the like may be mentioned as the methods other than the TEM-EDS measurement method. Further, the degree of precision of the solid solution ratio of the separated phthalocyanine obtained by the TEM-EDS analysis relative to the solid solution ratio thereof obtained by the ICP emission spectrometric analysis is within 20%, preferably within 10%, or more preferably within 5%. The ICP emission spectrometric analysis is to analyze the solid solution ratio of the separated phthalocyanine cluster, or in other words, the solid solution ratio of the separated phthalocyanine contained in powders or a dispersion solution of the separated phthalocyanine. Illustrative example of the analysis method other than the ICP emission spectrometric analysis includes a thermal analysis such as TG-DTA and DSC, IR and NMR (solution), gas chromatography, liquid chromatography, ion chromatography, XPS, SIMS, and TOF-SIMS.

Method for Producing the Highly Heat Resistant Phthalocyanine:

With regard to the method for producing the highly heat resistant phthalocyanine according to the present invention, the phthalocyanine can be produced by using an apparatus based on the principle described in Patent Document 3 filed by the Applicant of the present invention, as shown later.

In one example of the method for producing the highly heat resistant phthalocyanine according to the present invention wherein a fluid which contains the phthalocyanine solution having the phthalocyanine raw material dissolved into a solvent is mixed with a fluid which contains the phthalocyanine separating solvent thereby separating the phthalocyanine microparticles, the phthalocyanine microparticles are produced by the method wherein each of the above-mentioned fluids are mixed as a thin film fluid between processing surfaces which are disposed in a position they are faced with each other so as to be able to approach to and separate from each other, at least one of which rotates relative to the other, thereby separating the phthalocyanine microparticles in the said thin film fluid.

Hereunder, this production method will be explained. However, this production method is only one mere example; and thus, the present invention is not limited to this production method.

Hereunder, embodiments of the above-mentioned apparatus will be explained with referring to the drawings.

Figure 1:
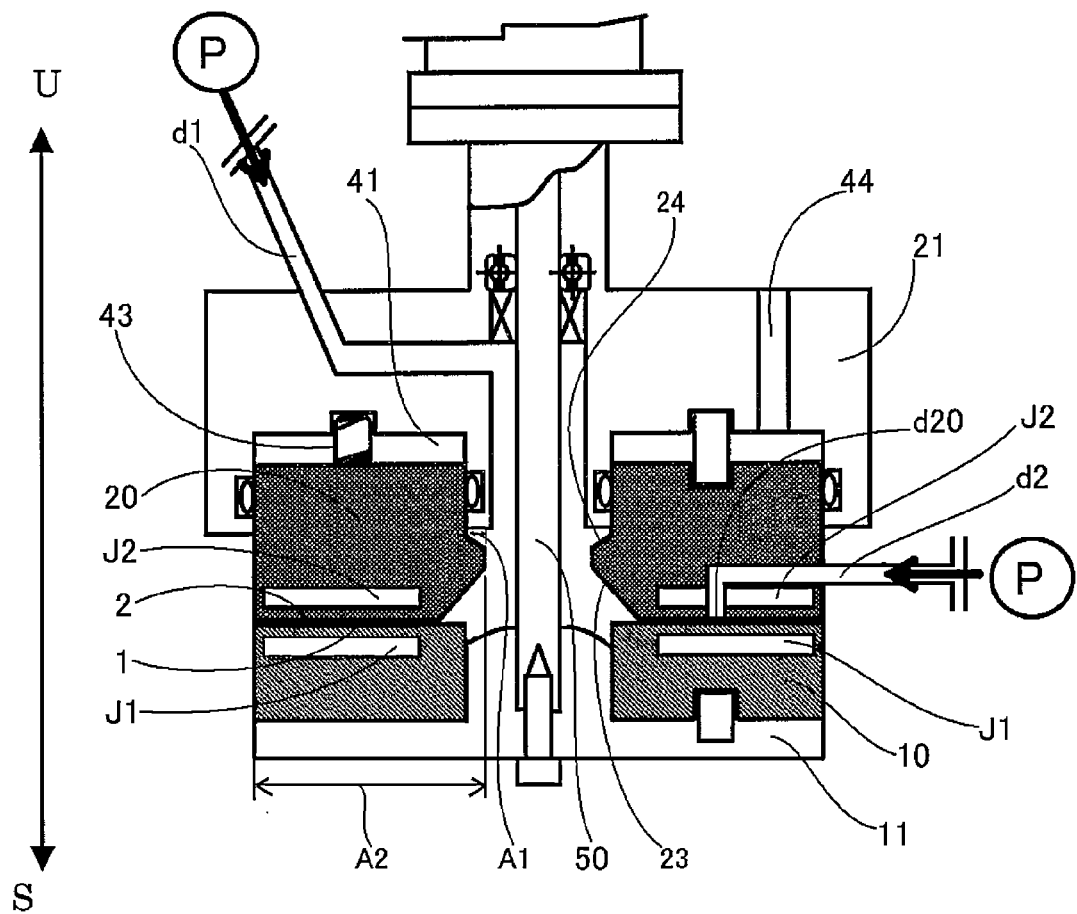
FIG. 1 is a schematic sectional view showing the fluid processing apparatus according to an embodiment of the present invention.
Figure 2:
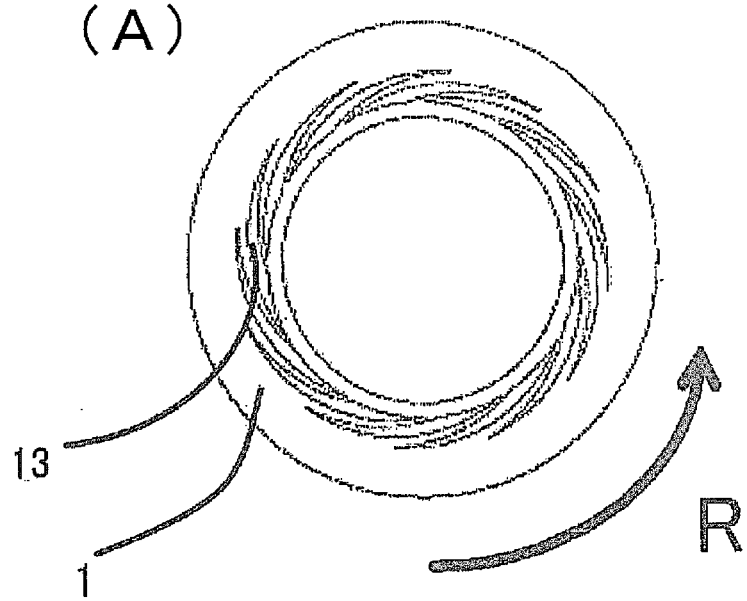
FIG. 2(A) is a schematic plane view of the first processing surface in the fluid processing apparatus shown in FIG. 1.
FIG. 2(B) is an enlarged view showing an important part of the processing surface in the apparatus.
Figure 2:
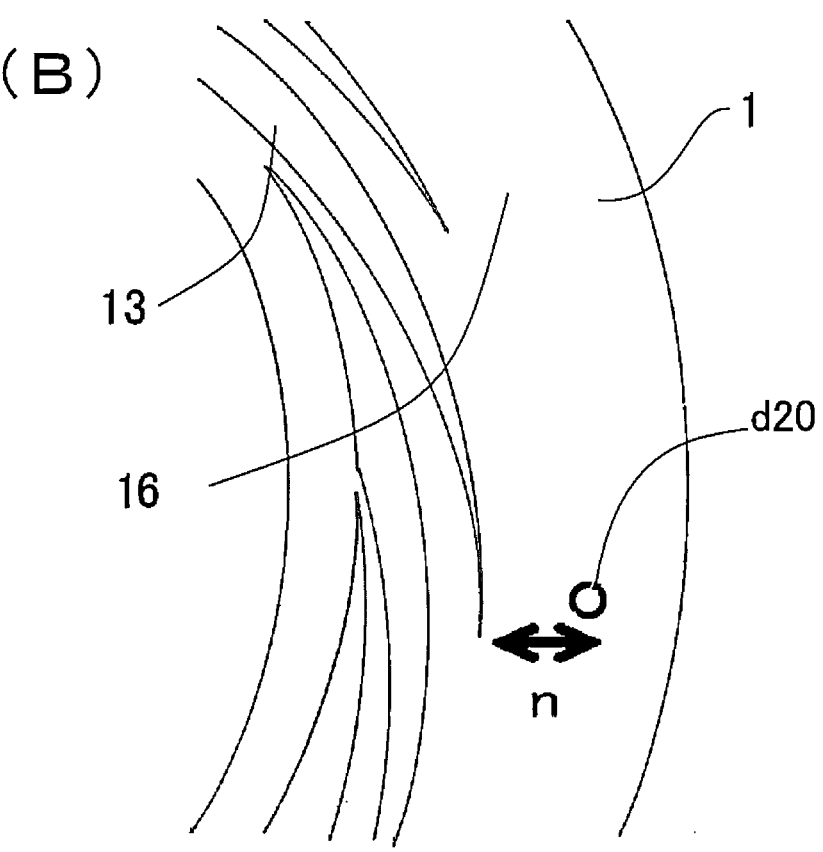
Figure 3:
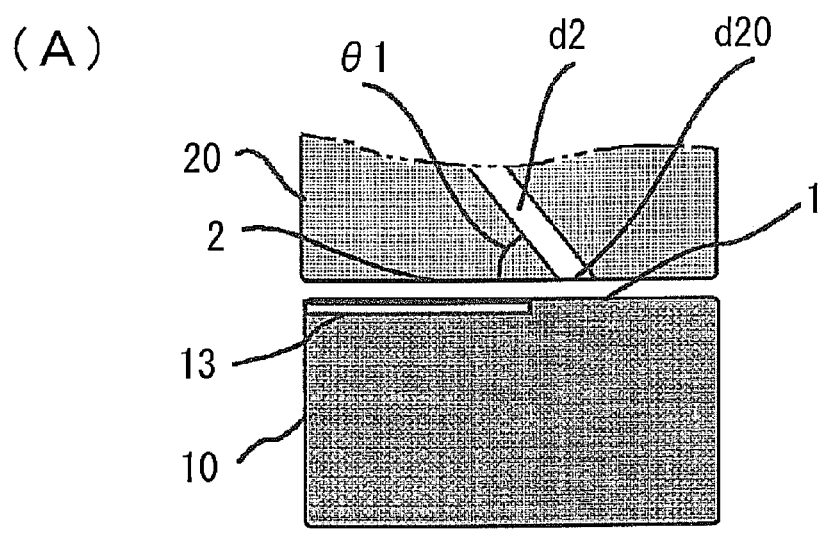
FIG. 3(A) is a sectional view of the second introduction member of the apparatus.
FIG. 3(B) is an enlarged view showing an important part of the processing surface for explaining the second introduction member.
Figure 3:
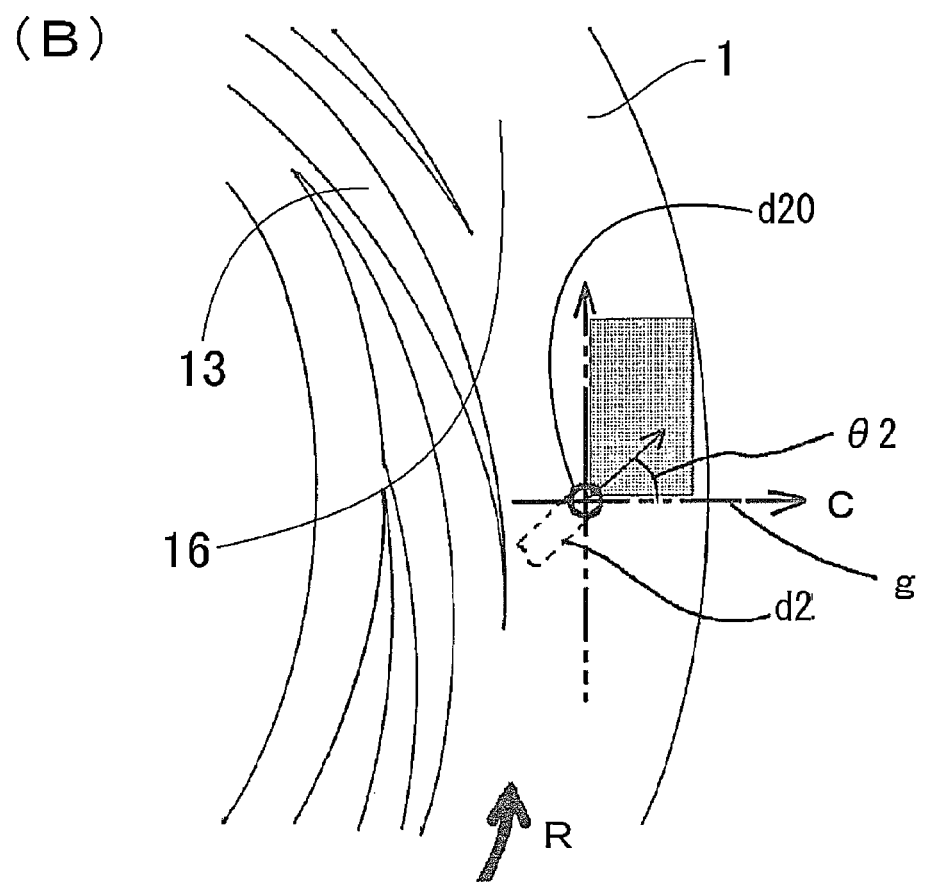

The fluid processing apparatus shown in FIG. 1 to FIG. 3 is similar to the apparatus described in Patent Document 5, with which a material to be processed is processed between processing surfaces in processing members arranged so as to be able to approach to and separate from each other, at least one of which rotates relative to the other; wherein, of the fluids to be processed, a first fluid to be processed, i.e., a first fluid, is introduced into between the processing surfaces, and a second fluid to be processed, i.e., a second fluid, is introduced into between the processing surfaces from a separate path that is independent of the flow path introducing the afore-mentioned first fluid and has an opening leading to between the processing surfaces, whereby the first fluid and the second fluid are mixed and stirred between the processing surfaces. Meanwhile, in FIG. 1, a reference character U indicates an upside and a reference character S indicates a downside; however, up and down, frond and back and right and left shown therein indicate merely a relative positional relationship and does not indicate an absolute position. In FIG. 2(A) and FIG. 3(B), reference character R indicates a rotational direction. In FIG. 3(C), reference character C indicates a direction of centrifugal force (a radial direction).

In this apparatus provided with processing surfaces arranged opposite to each other so as to be able to approach to and separate from each other, at least one of which rotates relative to the other, at least two kinds of fluids to be processed are used as the fluid to be processed, wherein at least one fluid thereof contains at least one kind of material to be processed, a thin film fluid is formed by converging the respective fluids between these processing surfaces, and the material to be processed is processed in this thin film fluid. With this apparatus, a plurality of fluids to be processed may be processed as mentioned above; but a single fluid to be processed may be processed as well.

This fluid processing apparatus is provided with two processing members of a first processing member 10 and a second processing member 20 arranged opposite to each other, wherein at least one of these processing members rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

The processing surfaces 1 and 2 are connected to a flow path of the fluid to be processed and constitute part of the flow path of the fluid to be processed. Distance between these processing surfaces 1 and 2 can be changed as appropriate; and thus, the distance thereof is controlled so as to form a minute space usually less than 1 mm, for example, in the range of about 0.1 m to about 50 m. With this, the fluid to be processed passing through between the processing surfaces 1 and 2 becomes a forced thin film fluid forced by the processing surfaces 1 and 2.

When a plurality of fluids to be processed are processed by using this apparatus, the apparatus is connected to a flow path of the first fluid to be processed whereby forming part of the flow path of the first fluid to be processed; and part of the flow path of the second fluid to be processed other than the first fluid to be processed is formed. In this apparatus, the two paths converge into one, and two fluids to be processed are mixed between the processing surfaces 1 and 2 so that the fluids may be processed by reaction and so on. It is noted here that the term "process(ing)" includes not only the embodiment wherein a material to be processed is reacted but also the embodiment wherein a material to be processed is only mixed or dispersed without accompanying reaction.

To specifically explain, this apparatus is provided with a first holder 11 for holding the first processing member 10, a second holder 21 for holding the second processing member 20, a surface-approaching pressure imparting mechanism, a rotation drive member, a first introduction part d1, a second introduction part d2, and a fluid pressure imparting mechanism p.

As shown in FIG. 2(A), in this embodiment, the first processing member 10 is a circular body, or more specifically a disk with a ring form. Similarly, the second processing member 20 is a disk with a ring form. A material of the processing members 10 and 20 is not only metal and carbon, but also ceramics, sintered metal, abrasion-resistant steel, sapphire, other metal subjected to hardening treatment, and rigid material subjected to lining, coating, or plating. In the processing members 10 and 20 of this embodiment, at least part of the first and the second surfaces 1 and 2 arranged opposite to each other is mirror-polished.

Roughness of this mirror polished surface is not particularly limited; but surface roughness Ra is preferably 0.01 m to 1.0 m, or more preferably 0.03 m to 0.3 m.

At least one of the holders can rotate relative to the other holder by a rotation drive mechanism such as an electric motor (not shown in drawings). A reference numeral 50 in FIG. 1 indicates a rotary shaft of the rotation drive mechanism; in this embodiment, the first holder 11 attached to this rotary shaft 50 rotates, and thereby the first processing member 10 attached to this first holder 11 rotates relative to the second processing member 20. As a matter of course, the second processing member 20 may be made to rotate, or the both may be made to rotate. Further in this embodiment, the first and second holders 11 and 21 may be fixed, while the first and second processing members 10 and 20 may be made to rotate relative to the first and second holders 11 and 21.

At least any one of the first processing member 10 and the second processing member 20 is able to approach to and separate from at least any other member, thereby the processing surfaces 1 and 2 are able to approach to and separate from each other.

In this embodiment, the second processing member 20 approaches to and separates from the first processing member 10, wherein the second processing member 20 is accepted in an accepting part 41 arranged in the second holder 21 so as to be able to rise and set. However, as opposed to the above, the first processing member 10 may approach to and separate from the second processing member 20, or both of the processing members 10 and 20 may approach to and separate from each other.

This accepting part 41 is a concave portion for mainly accepting that side of the second processing member 20 opposite to the second processing surface 2, and this concave portion is a groove being formed into a circle, i.e., a ring when viewed in a plane. This accepting part 41 accepts the second processing member 20 with sufficient clearance so that the second processing member 20 may rotate. Meanwhile, the second processing member 20 may be arranged so as to be movable only parallel to the axial direction; alternatively, the second processing member 20 may be made movable, by making this clearance larger, relative to the accepting part 41 so as to make the center line of the processing member 20 inclined, namely unparallel, to the axial direction of the accepting part 41, or movable so as to deviate the center line of the processing member 20 and the center line of the accepting part 41 toward the radius direction.

It is preferable that the second processing member 20 be accepted by a floating mechanism so as to be movable in the three dimensional direction, as described above.

The fluids to be processed are introduced into between the processing surfaces 1 and 2 from the first introduction part d1 and the second introduction part d2 under the state that pressure is applied thereto by a fluid pressure imparting mechanism p consisting of various pumps, potential energy, and so on. In this embodiment, the first introduction part d1 is a flow path arranged in the center of the circular second holder 21, and one end thereof is introduced into between the processing surfaces 1 and 2 from inside the circular processing members 10 and 20. Through the second introduction part d2, the second fluid to be processed for reaction to the first fluid to be processed is introduced into between the processing surfaces 1 and 2. In this embodiment, the second introduction part d2 is a flow path arranged inside the second processing member 20, and one end thereof is open at the second processing surface 2. The first fluid to be processed which is pressurized with the fluid pressure imparting mechanism p is introduced from the first introduction part d1 to the space inside the processing members 10 and 20 so as to pass through between the first and second processing surfaces 1 and 2 to outside the processing members 10 and 20. From the second introduction part d2, the second fluid to be processed which is pressurized with the fluid pressure imparting mechanism p is provided into between the processing surfaces 1 and 2, whereat this fluid is converged with the first fluid to be processed, and there, various fluid processing such as mixing, stirring, emulsification, dispersion, reaction, deposition, crystallization, and separation are effected, and then the fluid thus processed is discharged from the processing surfaces 1 and 2 to outside the processing members 10 and 20. Meanwhile, an environment outside the processing members 10 and 20 may be made negative pressure by a vacuum pump.

The surface-approaching pressure imparting mechanism mentioned above supplies the processing members with force exerting in the direction of approaching the first processing surface 1 and the second processing surface 2 each other. In this embodiment, the surface-approaching pressure imparting mechanism is arranged in the second holder 21 and biases the second processing member 20 toward the first processing member 10.

The surface-approaching pressure imparting mechanism is a mechanism to generate a force (hereinafter "surface-approaching pressure") to press the first processing surface 1 of the first processing member 10 and the second processing surface 2 of the second processing member 20 in the direction to make them approach to each other. By the balance between this surface-approaching pressure and the force to separate the processing surfaces 1 and 2 from each other, i.e., the force such as the fluid pressure, a thin film fluid having minute thickness in a level of nanometer or micrometer is generated. In other words, the distance between the processing surfaces 1 and 2 is kept in a predetermined minute distance by the balance between these forces.

In the embodiment shown in FIG. 1, the surface-approaching pressure imparting mechanism is arranged between the accepting part 41 and the second processing member 20. Specifically, the surface-approaching pressure imparting mechanism is composed of a spring 43 to bias the second processing member 20 toward the first processing member 10 and a biasing-fluid introduction part 44 to introduce a biasing fluid such as air and oil, wherein the surface-approaching pressure is provided by the spring 43 and the fluid pressure of the biasing fluid. The surface-approaching pressure may be provided by any one of this spring 43 and the fluid pressure of this biasing fluid; and other forces such as magnetic force and gravitation may also be used. The second processing member 20 recedes from the first processing member 10 thereby making a minute space between the processing surfaces by separating force, caused by viscosity and the pressure of the fluid to be processed applied by the fluid pressure imparting mechanism p, against the bias of this surface-approaching pressure imparting mechanism. By this balance between the surface-approaching pressure and the separating force as mentioned above, the first processing surface 1 and the second processing surface 2 can be set with the precision of a micrometer level; and thus the minute space between the processing surfaces 1 and 2 may be set. The separating force mentioned above includes fluid pressure and viscosity of the fluid to be processed, centrifugal force by rotation of the processing members, negative pressure when negative pressure is applied to the biasing-fluid introduction part 44, and spring force when the spring 43 works as a pulling spring. This surface-approaching pressure imparting mechanism may be arranged also in the first processing member 10, in place of the second processing member 20, or in both of the processing members.

To specifically explain the separation force, the second processing member 20 has the second processing surface 2 and a separation controlling surface 23 which is positioned inside the processing surface 2 (namely at the entering side of the fluid to be processed into between the first and second processing surfaces 1 and 2) and next to the second processing surface 2. In this embodiment, the separation controlling surface 23 is an inclined plane, but may be a horizontal plane. The pressure of the fluid to be processed acts to the separation controlling surface 23 to generate force directing to separate the second processing member 20 from the first processing member 10. Therefore, the second processing surface 2 and the separation controlling surface 23 constitute a pressure receiving surface to generate the separation force.

In the example shown in FIG. 1, an approach controlling surface 24 is formed in the second processing member 20. This approach controlling surface 24 is a plane opposite, in the axial direction, to the separation controlling surface 23 (upper plane in FIG. 1) and, by action of pressure applied to the fluid to be processed, generates force of approaching the second processing member 20 toward the first processing member 10.

Meanwhile, the pressure of the fluid to be processed exerted on the second processing surface 2 and the separation controlling surface 23, i.e., the fluid pressure, is understood as force constituting an opening force in a mechanical seal. The ratio (area ratio A1/A2) of a projected area A1 of the approach controlling surface 24 projected on a virtual plane perpendicular to the direction of approaching and separating the processing surfaces 1 and 2, that is, to the direction of rising and setting of the second processing member 20 (axial direction in FIG. 1), to a total area A2 of the projected area of the second processing surface 2 of the second processing member 20 and the separation controlling surface 23 projected on the virtual plane is called as balance ratio K, which is important for control of the opening force. This opening force can be controlled by the pressure of the fluid to be processed, i.e., the fluid pressure, by changing the balance line, i.e., by changing the area A1 of the approach controlling surface 24.

Sliding surface actual surface pressure P, i.e., the fluid pressure out of the surface-approaching pressures, is calculated according to the following equation:

$$P = P1 \times (K-k) + Ps$$

Here, P1 represents the pressure of a fluid to be processed, i.e., the fluid pressure, K represents the balance ratio, k represents an opening force coefficient, and Ps represents a spring and back pressure.

By controlling this balance line to control the sliding surface actual surface pressure P, the space between the processing surfaces 1 and 2 is formed as a desired minute space, thereby forming a fluid film of the fluid to be processed so as to make the processed substance such as a product fine and to effect uniform processing by reaction.

Meanwhile, the approach controlling surface 24 may have a larger area than the separation controlling surface 23, though this is not shown in the drawing.

The fluid to be processed becomes a forced thin film fluid by the processing surfaces 1 and 2 that keep the minute space therebetween, whereby the fluid is forced to move out from the circular, processing surfaces 1 and 2. However, the first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Meanwhile, a rotary shaft 50 is not only limited to be placed vertically, but may also be placed horizontally, or at a slant. This is because the fluid to be processed is processed in a minute space between the processing surfaces 1 and 2 so that the influence of gravity can be substantially eliminated. In addition, this surface-approaching pressure imparting mechanism can function as a buffer mechanism of micro-vibration and rotation alignment by concurrent use of the foregoing floating mechanism with which the second processing member 20 may be held displaceably.

In the first and second processing members 10 and 20, the temperature thereof may be controlled by cooling or heating at least any one of them; in FIG. 1, an embodiment having temperature regulating mechanisms J1 and J2 in the first and second processing members 10 and 20 is shown. Alternatively, the temperature may be regulated by cooling or heating the introducing fluid to be processed. These temperatures may be used to separate the processed substance or may be set so as to generate Benard convection or Marangoni convection in the fluid to be processed between the first and second processing surfaces 1 and 2.

As shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1 as shown in FIG. 2(B), or, though not shown in the drawing, may be extended straight radially, or bent at a right angle, or jogged; and the depression may be continuous, intermittent, or branched. In addition, this depression 13 may be formed also on the second processing surface 2, or on both of the first and second processing surfaces 1 and 2. By forming the depression 13 as mentioned above, the micro-pump effect can be obtained so that the fluid to be processed may be sucked into between the first and second processing surfaces 10 and 20.

The base end of the depression 13 reaches preferably inner circumference of the first processing member 10. The front end of the depression 13 extends in an outer circumferential direction of the first processing surface 1 with the depth thereof (cross-sectional area) being gradually shallower as going from the base end toward the front end.

Between the front end of the depression 13 and the outer periphery of the first processing surface 1 is arranged a flat surface 16 not having the depression 13.

When an opening d20 of the second introduction part d2 is arranged in the second processing surface 2, the arrangement is done preferably at a position opposite to the flat surface 16 of the first processing surface 1 arranged at a position opposite thereto.

This opening d20 is arranged preferably in the downstream (outside in this case) of the depression 13 of the first processing surface 1. The opening is arranged especially preferably at a position opposite to the flat surface 16 located nearer to the outer diameter than a position where the direction of flow upon introduction by the micro-pump effect is changed to the direction of a spiral and laminar flow formed between the processing surfaces. Specifically, in FIG. 2(B), a distance n from the outermost side of the depression 13 arranged in the first processing surface 1 in the radial direction is preferably about 0.5 mm or more. Especially in the case of separating microparticles from a fluid, it is preferable that mixing of a plurality of fluids to be processed and separation of the microparticles therefrom be effected under the condition of a laminar flow.

Shape of the opening d20 may be circular as shown in FIG. 2(B) and FIG. 3(B); or though not shown by a drawing, it may be a concentric circular ring which encloses the opening in the central part of the processing surface 2 having a ring-like disk shape. If the opening is in the shape of the circular ring, this circular ring opening may be continuous or discontinuous.

This second introduction part d2 may have directionality. For example, as shown in FIG. 3(A), the direction of introduction from the opening d20 of the second processing surface 2 is inclined at a predetermined elevation angle ($\theta 1$) relative to the second processing surface 2. The elevation angle ($\theta 1$) is set at more than 0° and less than 90°, and when the reaction speed is high, the angle ($\theta 1$) is preferably set in the range of 1° to 45°.

In addition, as shown in FIG. 3(B), introduction from the opening d20 of the second processing surface 2 has directionality in a plane along the second processing surface 2. The direction of introduction of this second fluid is in the outward direction departing from the center in a radial component of the processing surface and in the forward direction in a rotation component of the fluid between the rotating processing surfaces. In other words, a predetermined angle ($\theta 2$) exists facing the rotation direction R from a reference line g, which is the line to the outward direction and in the radial direction passing through the opening d20. This angle ($\theta 2$) is also set preferably at more than 0° and less than 90°.

This angle ($\theta 2$) can vary depending on various conditions such as the type of fluid, the reaction speed, viscosity, and the rotation speed of the processing surface. In addition, it is also possible not to give the directionality to the second introduction part d2 at all.

In the embodiment shown in FIG. 1, kinds of the fluid to be processed and numbers of the flow path thereof are set two respectively; but they may be one, or three or more. In the embodiment shown in FIG. 1, the second fluid is introduced into between the processing surfaces 1 and 2 from the introduction part d2; but this introduction part may be arranged in the first processing member 10 or in both. Alternatively, a plurality of introduction parts may be arranged relative to one fluid to be processed. The opening for introduction arranged in each processing member is not particularly restricted in its form, size, and number; and these may be changed as appropriate. The opening of the introduction part may be arranged just before the first and second processing surfaces 1 and 2 or in the side of further upstream thereof.

To effect the reaction between the processing surfaces 1 and 2, the second fluid may be introduced through the first introduction part d1 and the first fluid through the second introduction part d2, as opposed to the above description. That is, the expression "first" or "second" for each solvent has a meaning for merely discriminating an $n^{th}$ solvent among a plurality of solvents present, and third or more solvents can also be present.

In the apparatus mentioned above, a treatment such as separation/precipitation and crystallization is done while effecting forced and uniform mixing between the processing surfaces 1 and 2 which are disposed in a position they are faced with each other so as to be able to approach to and separate from each other, at least one of which rotates relative to the other, as shown in FIG. 1. The particle diameter and the monodispersity of the processed material to be processed can be controlled by appropriately controlling rotation speed of the processing members 10 and 20, flow rate, distance between the processing surfaces 1 and 2, concentration of raw materials in the fluids to be processed, kind of solvents in the fluids to be processed, and so forth.

Hereunder, specific embodiments of the method for producing the highly heat resistant phthalocyanine microparticles by using the apparatus shown above will be explained.

In the apparatus shown above, the highly heat resistant phthalocyanine is separated by mixing, as the fluids to be processed, the phthalocyanine solution with the phthalocyanine separating solvent in a thin film fluid formed between the processing surfaces 1 and 2 which are disposed in a position they are faced with each other so as to be able to approach to and separate from each other, at least one of which rotates relative to the other.

The separation reaction of the highly heat resistant phthalocyanine takes place in the apparatus as shown in FIG. 1 while effecting forced and uniform mixing between the processing surfaces 1 and 2 which are disposed in a position they are faced with each other so as to be able to approach to and separate from each other, at least one of which rotates relative to the other.

At first, from the first introduction part d1, which is one flow path, the phthalocyanine separating solvent as the first fluid is introduced into between the processing surfaces 1 and 2 which are disposed in a position they are faced with each other so as to be able to approach to and separate from each other, at least one of which rotates relative to the other, thereby forming between the processing surfaces a first thin film fluid which is the thin film fluid constituted of the first fluid.

Then, from the second introduction part d2, which is another flow path, the phthalocyanine solution as the second fluid is introduced directly into the first thin film fluid formed between the processing surfaces 1 and 2.

By so doing, the first fluid and the second fluid are mixed between the processing surfaces 1 and 2 whose distance is fixed by the pressure balance between the supply pressure of the fluids to be processed and the pressure applied between the rotating processing surfaces, thereby effecting the separation reaction of the highly heat resistant phthalocyanine microparticles.

Combination of the first fluid and the second fluid is not particularly restricted; a fluid which contains a phthalocyanine solution having a phthalocyanine raw material dissolved in a solvent and a fluid which contains a phthalocyanine separating solvent may be used. The phthalocyanine separating solvent is defined as that this solvent is capable of becoming a poor solvent which has lower solubility to the phthalocyanine raw material than the solvent in which the phthalocyanine raw material is dissolved.

Of the highly heat resistant phthalocyanines according to the present invention, the solid solution ratio in the phthalocyanine microparticles that are separated by mixing of the phthalocyanine solution having two or more phthalocyanine raw materials dissolved therein with the phthalocyanine separating solvent can be readily controlled by changing the introduction ratio (ratio such as the weight ratio and the mol ratio) of two or more different phthalocyanine raw materials in the phthalocyanine solution to be introduced into between the processing surfaces 1 and 2. To change the introduction ratio of two or more different phthalocyanine raw materials in the phthalocyanine solution to be introduced into between the processing surfaces 1 and 2, any one of the introduction rate of the phthalocyanine solution into between the processing surfaces 1 and 2 and concentration of the phthalocyanine raw material in the phthalocyanine solution or both may be changed.

For example, in the case that the phthalocyanine solution obtained by dissolving two or more phthalocyanine raw materials into a solvent is introduced into between the processing surfaces 1 and 2, concentration of the phthalocyanine raw material in the phthalocyanine solution may be changed while the introduction rate of the phthalocyanine solution into between the processing surfaces 1 and 2 is kept constant, or the introduction rate of the phthalocyanine solution into between the processing surfaces 1 and 2 may be changed while concentration of the phthalocyanine raw material in the phthalocyanine solution that is introduced therebetween is kept constant. Alternatively, both the introduction rate of the phthalocyanine solution into between the processing surfaces 1 and 2 and concentration of the phthalocyanine raw material in the phthalocyanine solution may be changed.

Further, illustrative example thereof includes a method in which concentration of the phthalocyanine raw material in the phthalocyanine solution is changed by diluting the phthalocyanine solution just before it is introduced into between the processing surfaces 1 and 2 or just before it is mixed with the phthalocyanine separating solvent.

To introduce the phthalocyanine solution into between the processing surfaces 1 and 2, as mentioned above, the phthalocyanine solution having two or more phthalocyanine raw materials dissolved into a solvent may be introduced into between the processing surfaces 1 and 2; or in other embodiment, after a plurality of solutions, having phthalocyanine raw material dissolved therein, such as a first phthalocyanine solution and a second phthalocyanine solution in which two or more phthalocyanine raw materials are dissolved into respective solvents are prepared, they are mixed before introduction into between the processing surfaces 1 and 2 in such a manner that an intended solid solution ratio may be obtained thereby preparing the phthalocyanine solution having two or more phthalocyanine raw materials dissolved thereinto, and then, the solution thus prepared may be introduced into the processing surfaces 1 and 2.

To effect the reaction between the processing surfaces 1 and 2, the second fluid may be introduced through the first introduction part d1 and the first fluid through the second introduction part d2, as opposed to the above description. That is, the expression "first" or "second" for each solvent has a meaning for merely discriminating an $n^{th}$ solvent among a plurality of solvents present, and third or more solvents can also be present.

As mentioned before, the processing apparatus may be provided with, in addition to the first introduction part d1 and the second introduction part d2, the third introduction part d3; and in this case, for example, each of the first fluid, the second fluid, and the third fluid may be introduced separately into the processing apparatus. By so doing, concentration and pressure of each fluid can be controlled separately so that the separation reaction and stabilization of particle diameter of the separated phthalocyanine microparticles may be controlled more precisely. Meanwhile, a combination of the fluids to be processed (first to third fluids) that are introduced into each of the introduction parts may be set arbitrarily. The same is applied if the fourth or more introduction parts are arranged; and by so doing, fluids to be introduced into the processing apparatus may be subdivided.

In addition, temperatures of the fluids to be processed such as the first fluid, the second fluid, and so on may be controlled; and temperature difference among the first fluid, the second fluid, and so on (namely, temperature difference among each of the supplied fluids to be processed) may be controlled either. To control temperature and temperature difference of each of the supplied fluids to be processed, a mechanism with which temperature of each of the fluids to be processed is measured (temperature of the fluid before introduction to the processing apparatus, or in more detail, just before introduction into between the processing surfaces 1 and 2) so that each of the fluids to be processed that is introduced into between the processing surfaces 1 and 2 may be heated or cooled may be installed.

As to the solvent to dissolve the phthalocyanine raw material, there is no particular restriction, while illustrative example of an aqueous acidic solution usable therein includes sulfuric acid, hydrochloric acid, nitric acid, trifluoroacetic acid, phosphoric acid, fuming sulfuric acid, and fuming nitric acid. Especially in the case that a surface-treated copper phthalocyanine microparticle is produced, fuming sulfuric acid and fuming nitric acid are preferable. Other illustrative example of the usable solvent includes an amide solvent such as 1-methyl-2-pyrrolidinone, 1,3-dimethyl-2-imidazolidinone, 2-pyrrolidinone, ε-caprolactam, formamide, N-methyl formamide, N,N-dimethyl formamide, acetamide, N-methyl acetamide, N,N-dimethyl acetamide, N-methyl propanamide, and hexamethyl phosphoric triamide; dimethyl sulfoxide and pyridine; and a mixture of these solvents. Alternatively, a phthalocyanine solution having the phthalocyanine raw material dissolved into a solution which is obtained by adding a basic or an acidic substance into various organic solvents may also be used. Illustrative example of the basic substance that can be added to the foregoing organic solvents includes sodium hydroxide, potassium hydroxide, sodium methoxide, and sodium ethoxide. Illustrative example of the acidic substance includes, similarly to the above-mentioned, sulfuric acid, hydrochloric acid, nitric acid, trifluoroacetic acid, and phosphoric acid.

As to the phthalocyanine separating solvent, a solvent having lower solubility to the phthalocyanine raw material than the solvent into which the phthalocyanine raw material has been dissolved can be used. Illustrative example of the solvent like this includes water, an alcohol compound solvent, an amide compound solvent, a ketone compound solvent, an ether compound solvent, an aromatic compound solvent, carbon disulfide, an aliphatic compound solvent, a nitrile compound solvent, a sulfoxide compound solvent, a halogenated compound solvent, an ester compound solvent, a pyridine compound solvent, an ionic liquid solvent, a carboxylic acid compound solvent, a sulfonic acid compound solvent, and a sulfolane compound solvent. These solvents may be used singly or as a mixture of two or more of them.

To explain the above-mentioned solvents in more detail, illustrative example of water includes tap water, ion-exchanged water, pure water, ultrapure water, and RO water; illustrative example of the alcohol compound solvent includes methanol, ethanol, isopropanol, n-propanol, and 1-methoxy-2-propanol; and in addition, a linear alcohol such as n-butanol; a branched alcohol such as 2-butanol and tert-butanol; a polyvalent alcohol such as ethylene glycol and diethylene glycol; and propylene glycol monomethyl ether. Illustrative example of the ketone compound solvent includes acetone, methyl ethyl ketone, and cyclohexanone. Illustrative example of the ether compound solvent includes dimethyl ether, diethyl ether, and tetrahydrofuran. Illustrative example of the aromatic compound solvent includes benzene, toluene, xylene, nitrobenzene, chlorobenzene, and dichlorobenzene. Illustrative example of the aliphatic compound solvent includes hexane. Illustrative example of the nitrile compound solvent includes acetonitrile. Illustrative example of the sulfoxide compound solvent includes dimethyl sulfoxide, diethyl sulfoxide, hexamethylene sulfoxide, and sulfolane. Illustrative example of the halogen-containing compound solvent includes chloroform, dichloromethane, trichloroethylene, and iodoform. Illustrative example of the ester compound solvent includes ethyl acetate, butyl acetate, methyl lactate, ethyl lactate, and 2-(1-methoxy) propyl acetate. Illustrative example of the ionic liquid includes a salt of 1-butyl-3-methyl imidazolium with PF6 (hexafluorophosphate ion). Illustrative example of the amide compound solvent includes N, N-dimethyl formamide, 1-methyl-2-pyrrolidone, 2-pyrrolidinone, 1,3-dimethyl-2-imidazolidinone, 2-pyrrolidinone, ε-caprolactam, formamide, N-methyl formamide, acetamide, N-methyl acetamide, N,N-dimethyl acetamide, N-methylpropane amide, and hexamethyl phosphoric triamide. Illustrative example of the carboxylic acid compound includes 2,2-dichloropropionic acid and squaric acid. Illustrative example of the sulfonic acid compound includes methanesulfonic acid, p-toluenesulfonic acid, chlorosulfonic acid, and trifluoromethane sulfonic acid.

In addition, a dispersing agent such as a block copolymer, a polymer, and a surfactant may be contained in the fluid which contains the phthalocyanine solution, or in the fluid which contains the phthalocyanine separating solvent, or in both of these fluids. Alternatively, this dispersing agent may be contained in the third fluid which is different from any of the fluid which contains the phthalocyanine solution and the fluid which contains the phthalocyanine separating solvent.

As surfactants and dispersing agent, various commercial products for use in dispersion of pigments can be used. The surfactants and dispersants include, but are not limited to, those based on dodecylbenzenesulfonic acid such as sodium dodecyl sulfate or Neogen R-K (manufactured by Dai-ichi Kogyo Seiyaku Co., Ltd.), Solsperse 20000, Solsperse 24000, Solsperse 26000, Solsperse 27000, Solsperse 28000, and Solsperse 41090 (manufactured by Avecia Corporation), Disperbyk-160, Disperbyk-161, Disperbyk-162, Disperbyk-163, Disperbyk-166, Disperbyk-170, Disperbyk-180, Disperbyk-181, Disperbyk-182, Disperbyk-183, Disperbyk-184, Disperbyk-190, Disperbyk-191, Disperbyk-192, Disperbyk-2000, and Disperbyk-2001 (manufactured by BYK-Chemie), Polymer 100, Polymer 120, Polymer 150, Polymer 400, Polymer 401, Polymer 402, Polymer 403, Polymer 450, Polymer 451, Polymer 452, Polymer 453, EFKA-46, EFKA-47, EFKA-48, EFKA-49, EFKA-1501, EFKA-1502, EFKA-4540, and EFKA-4550 (manufactured by EFKA Chemical Corp.), Flowlen DOPA-158, Flowlen DOPA-22, Flowlen DOPA-17, Flowlen G-700, Flowlen TG-720W, Flowlen-730W, Flowlen-740W, and Flowlen 745W (manufactured by Kyoeisha Chemical Co., Ltd.), Ajisper PA-111, Ajisper PB-711, Ajisper PB-811, Ajisper PB-821, and Ajisper PW-911 (manufactured by Ajinomoto Co. Inc.), Johncryl 678, Johncryl 679, and Johncryl 62 (manufactured by Johnson Polymer B.V., and AQUALON KH-10, HITENOL NF-13 (manufactured by Dai-ichi Kogyo Seiyaku Co., Ltd.). These products may be used alone or in combination of two or more thereof.

The highly heat resistant phthalocyanine according to the present invention is the phthalocyanine that is separated by mixing a phtalocyanine solution having a phthalocyanine raw material dissolved therein with a phthalocyanine separating solvent; and it is confirmed that a decomposition temperature of the separated phthalocyanine is higher by 10° C. or more than a decomposition temperature of the phthalocyanine raw material, thereby having high heat resistance.

Application:

The highly heat resistant phthalocyanine according to the present invention can be applied to various uses such as a paint, an ink for an ink jet, a thermal transfer ink, a toner, a colored resin, a color filter, a catalyst, a charge generating material like an organic photoconductor, a semiconductor, and a solar cell.

EXAMPLES

Hereunder, Examples of producing the highly heat resistant phthalocyanine by using an apparatus based on the same principle as disclosed in the Patent Document 3 which was filed by the Applicant of the present invention will be shown. However, the present invention is not limited to the following Examples.

By using the apparatus as shown in FIG. 1 with which uniform stirring and mixing are effected in a thin film fluid formed between the processing surfaces 1 and 2 which are disposed in a position they are faced with each other so as to be able to approach to and separate from each other, at least one of which rotates relative to the other, a phthalocyanine solution having any one of a copper phthalocyanine (hereinafter Cu—Pc) and a brominated chlorinated zinc phthalocyanine (hereinafter Zn—Pc) or both dissolved in a solvent and a phthalocyanine separating solvent are converged together in the thin film fluid and mixed uniformly in the thin film fluid thereby separating the phthalocyanine microparticles.

In the following examples, the term "from the center" means "through the first introduction part d1" in the processing apparatus shown in FIG. 1, the first fluid refers to the first processed fluid, and the second fluid refers to the second processed fluid introduced "through the second introduction part d2" in the processing apparatus shown in FIG. 1. Additionally, "%" indicates "% by weight" in this context.

Prescribed amounts of the phthalocyanine raw materials shown in Table 1, i.e., Cu—Pc and Zn—Pc, were weighed into a vessel having a lid; and a mixed solution of fuming sulfuric acid and concentrated sulfuric acid (5% by weight of $SO_3$ and 95% by weight of $H_2SO_4$) was added thereinto. Thereafter, the vessel was capped with the lid, and then, the resulting mixture was dissolved by stirring with a stirrer for 5 minutes to prepare the phthalocyanine solution.

Pure water as the first fluid used as the phthalocyanine separating solvent was fed from the center into between the processing surfaces 1 and 2 with supply pressure of 0.3 MPaG and back pressure of 0.02 MPaG, and the above-prepared phthalocyanine solution as the second fluid was introduced into between the processing surfaces 1 and 2. The first fluid and the second fluid were mixed in the thin film fluid to separate phthalocyanine microparticles. The supply temperatures of the first fluid and the second fluid were measured respectively just before introduction into the processing apparatus (more precisely, just before introduction into between the processing surfaces 1 and 2). Experimental conditions are shown in Table 1. The ratio of Cu—Pc increases in the order from Example 1 to Example 5. In Example 1 and in Example 5, phthalocyanine microparticles only comprised of Zn—Pc or Cu—Pc, respectively, were prepared. Nos. 1, 2, 3, 4, and 5 in FIG. 6 and FIG. 7 correspond to Examples 1, 2, 3, 4, and 5, respectively.

persion solution. Apart of the aqueous paste of the phthalocyanine microparticles after washing was dried at 60° C. and −0.10 MPaG to obtain powders of the phthalocyanine microparticles; and this was used as the sample for the ICP analysis and for the TG/DTA analysis.

Measurement Instruments:

Measurement of the particle size distribution was done by using the dynamic photo-scattering particle size distribution measurement instrument Nanotrac UPA-UT151 (manufactured by Nikkiso Co., Ltd.); and with this, the dispersed particle diameter of the phthalocyanine microparticles was measured. The measurement conditions were: the particle refractive index of 1.81, the particle specific gravity of 1.0 g/cm³, the measurement solvent of pure water, and the measurement time of two minutes.

Observation of the form of the phthalocyanine microparticles was done by using the transmission electron microscope (TEM) JEM-2100 (manufactured by JEOL Ltd.) to evaluate the primary particle diameter thereof. In the EDS analysis, JEM-2100 (manufactured by JEOL Ltd.) arranged with the energy dispersive X-ray spectrometry instrument JED-2300 (manufactured by JEOL Ltd.) was used; and with this, quantitative analyses of Cu and Zn in the primary particles were carried out. The observation sample was prepared by dripping the phthalocyanine microparticle dispersion solution having pigment concentration of the phthalocyanine microparticles adjusted to 0.005% by weight onto a Mo grid attached with a collodion film followed by drying

TABLE 1

| | | Second fluid | | | | Processing condition | | |
|---|---|---|---|---|---|---|---|---|
| | | | | | | | Flow rate | Flow rate | Temperature |
| Example | First fluid | Phthalocyanine concentration (% by weight) | Cu—Pc:Zn—Pc (mol ratio) | | Solvent | Rotation speed (rpm) | of first fluid (mL/minute) | of second fluid | (first fluid/ second fluid) (° C.) |
| 1 | Pure water | 3 | 0 | 100 | 5% by weight $SO_3$— 95% by weight $H_2SO_4$ (98% by weight) | 1700 | 400 | 3 | 5/25 |
| 2 | | | 38 | 62 | | | | | |
| 3 | | | 58 | 42 | | | | | |
| 4 | | | 76 | 24 | | | | | |
| 5 | | | 100 | 0 | | | | | |

The aqueous dispersion solution of the phthalocyanine microparticles discharged from between the processing surfaces 1 and 2 was centrifugally separated by using the centrifugal separator 778011 (manufactured by Kubota Corp.) for 10 minutes with 23,000 G; and then, the solid-liquid separation was done by removing the supernatant solution with decantation. Subsequently, pure water was added into the deposited phthalocyanine microparticles; and then, after the resulting mixture was redispersed for 10 minutes by using the ultrasonic bath AU308CB (manufactured by Tokyo Rikakikai Co., Ltd.), operation of the centrifugal separation was repeated for three times to wash the phthalocyanine microparticles. The aqueous paste of the phthalocyanine microparticles after washing was added into an aqueous solution of 0.05% by weight of sodium dodecylsulfate (SDS) in such a manner that the pigment concentration therein might become 0.1% by weight. The resulting mixture was then subjected to dispersion treatment by using the ultrasonic disperser UP200S (manufactured by Hielscher Ultrasonics GmbH). Samples for the later-mentioned TEM and STEM-EDS analyses were prepared by using this disit under vacuum. The observation condition with the observation magnification of 500,000 or more was employed; and the average value of ten spots was used.

For element mapping and quantitative analyses of Cu, Zn, and Br in the particles by the energy dispersive X-ray spectrometry under the observation with the scanning transmission electron microscope (STEM-EDS), TITAN 80-300 (manufactured by FEI Company) attached with the γ-TEM EDS detector (manufactured by Ametek Inc.) was used.

For quantitative analyses of Cu and Zn contained in the powder sample by using the inductively coupled plasma emission spectro-photometry (ICP), ICP 8100 (manufactured by Shimadzu Corp.) was used. Observation wavelengths of 224.700 nm for Cu and 213.856 nm for Zn were used: and the evaluation thereof was done by the average value of three measurements.

For the differential thermogravimetry (TG/DTA) in the simultaneous measurements of thermogravimetry and differential thermal, TG/DTA-6300 (manufactured by Seiko Instruments Inc.) was used. The measurements thereof were done under an atmospheric condition with the temperature rising rate of 5° C. per one minute while using the reference sample of α-alumina and the sample weight of 10 mg (±0.5 mg).

Figure 6:
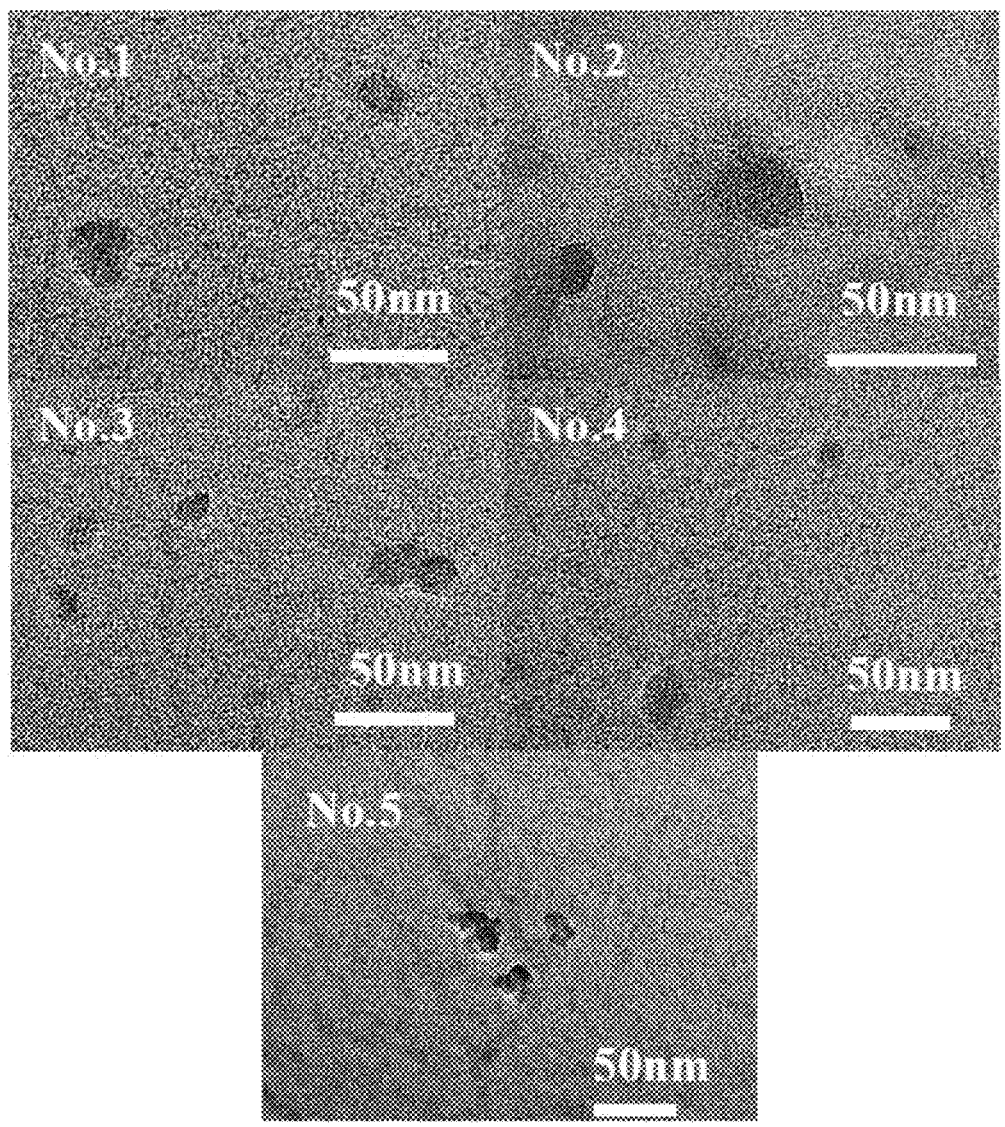
Figure 7:
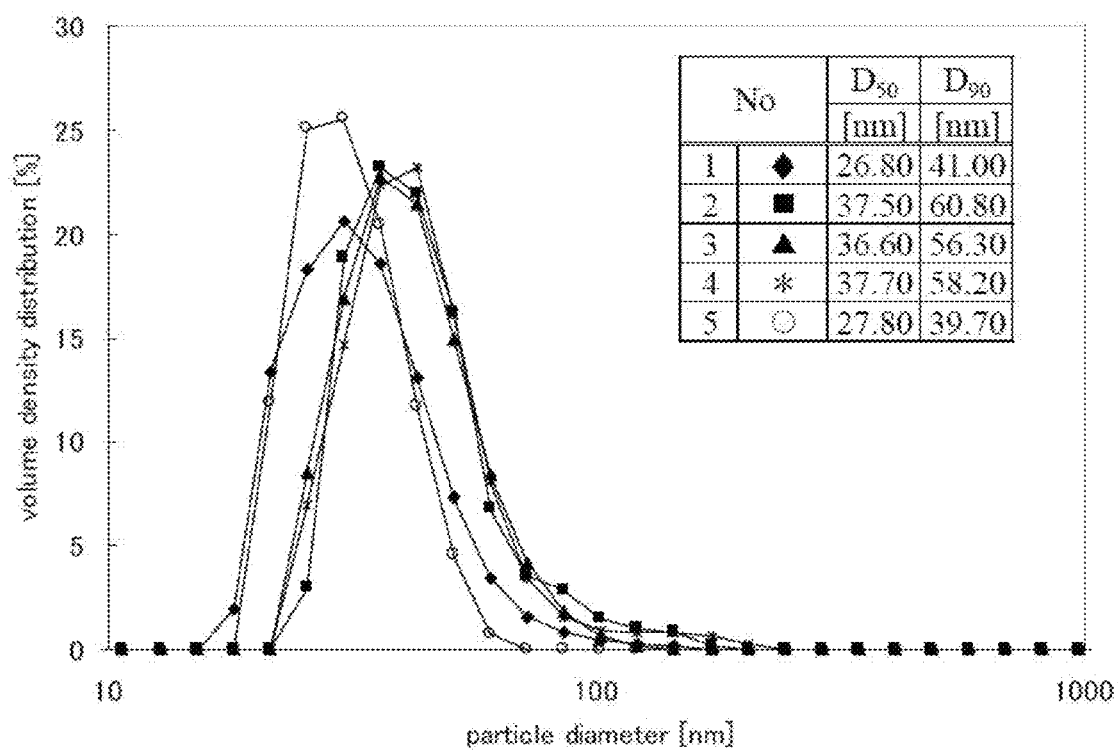

The TEM pictures and the particle size distribution measurement results of the prepared phthalocyanine microparticles are shown in FIG. 6 and FIG. 7. It was confirmed that the prepared phthalocyanine microparticles are nearly spherical particles having the primary particle diameter of about 10 to 30 nm. Further in addition, in the particle size distribution measurement results, it was confirmed that almost all of the phthalocyanine microparticles obtained in Examples had the particle diameter of 100 nm or less.

Figure 8:
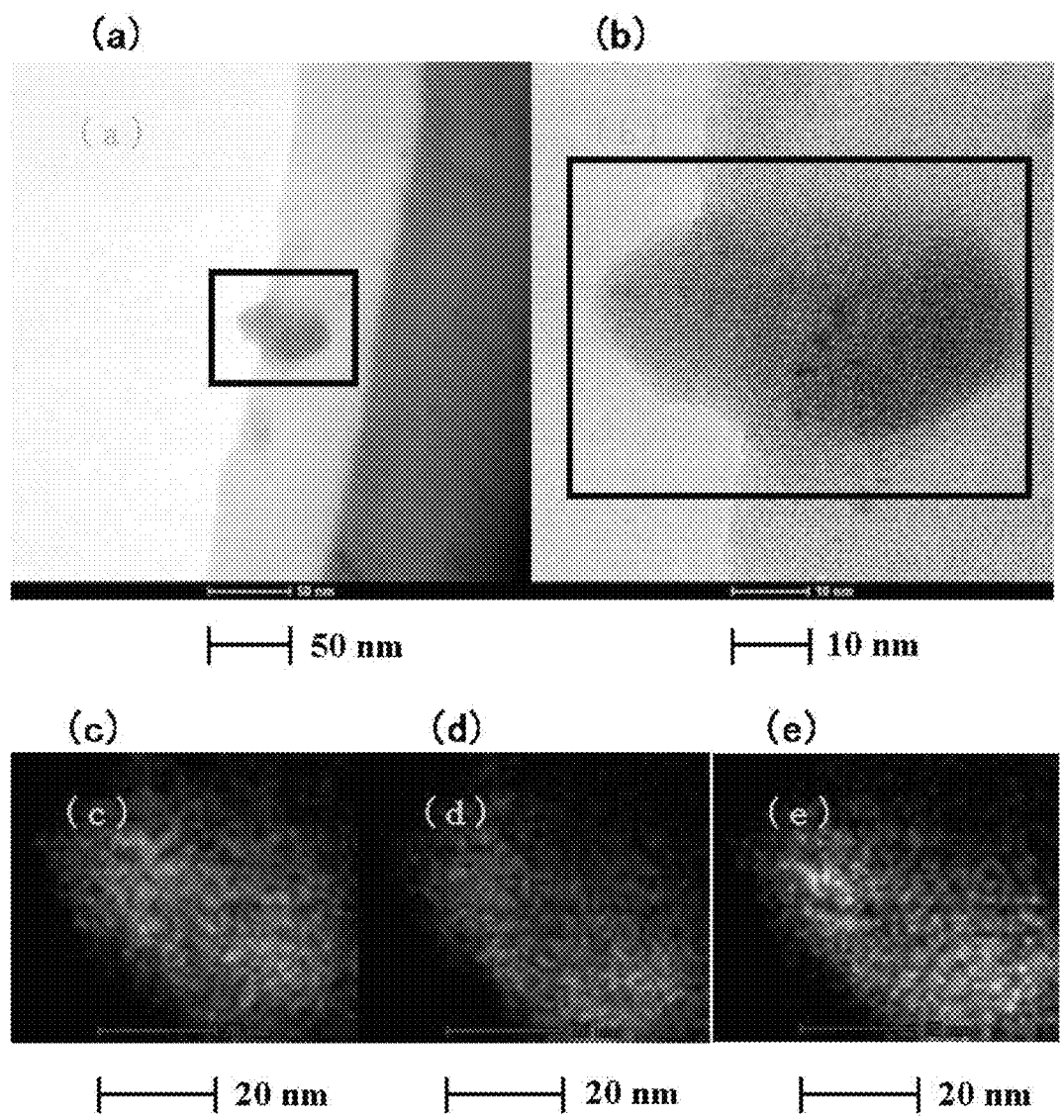

Then, elemental analyses of the prepared phthalocyanine microparticles were done. In FIG. 8, the STEM-EDS analysis results of the phthalocyanine microparticles prepared under the conditions of Example 3 are shown. In (a) and (b) of FIG. 8, the high resolution TEM (HRTEM) pictures are shown, wherein the areas enclosed by rectangles in (a) and (b) are mapping areas. The mapping picture of bromine (Br) is shown in (c), the mapping picture of copper (Cu) is shown in (d), and the mapping picture of zinc (Zn) is shown in (e). From the above analysis results, it was confirmed that Cu, Zn, and Br were not segregated but distributed uniformly. It was observed that the phthalocyanine microparticles prepared in Examples 2 and Example 4 were distributed similarly to those in Example 3.

Next, the ICP analysis of the prepared phthalocyanine microparticles was done. The ratios of Cu to Zn (mol ratio) obtained from the results thereof and the STEM-EDS analyses are shown in Table 2. The results of the ICP analysis and the STEM-EDS analysis almost agreed. From these results, it was confirmed that the prepared phthalocyanine microparticles were not segregated but formed as a solid solution.

In Table 2, the ratios of Cu to Zn (molar ratio) in the primary particles of the phthalocyanine microparticles prepared in Example 2 to Example 4, namely, the solid solution ratios and the degrees of precision obtained by the TEM-EDS analysis and the STEM-EDS analysis are shown. Each of the results almost agreed in their values. From these results, it was confirmed that the phthalocyanine microparticles having the uniform and homogenous solid solution ratio could be prepared. In addition, it was confirmed that the solid solution ratio of the phthalocyanine microparticles could be controlled by changing the ratio of two or more phthalocyanine raw materials introduced into between the processing surfaces 1 and 2.

TABLE 2

| | ICP | | STEM-EDS | | | TEM-EDS | | |
|---|---|---|---|---|---|---|---|---|
| Example | Cu (mol ratio) | Zn (mol ratio) | Cu (mol ratio) | Zn (mol ratio) | Degree of Precision (%) | Cu (mol ratio) | Zn (mol ratio) | Degree of Precision (%) |
| 1 | 0 | 100 | — | — | — | — | — | — |
| 2 | 38 | 62 | 40 | 60 | ±15.6 | 41.6 | 58.4 | ±1.13 |
| 3 | 58 | 42 | 60 | 40 | ±4.13 | 59.8 | 40.2 | ±12.0 |
| 4 | 76 | 24 | 70 | 30 | ±1.14 | 72.1 | 27.9 | ±5.64 |
| 5 | 100 | 0 | — | — | — | — | — | — |

Figure 9:
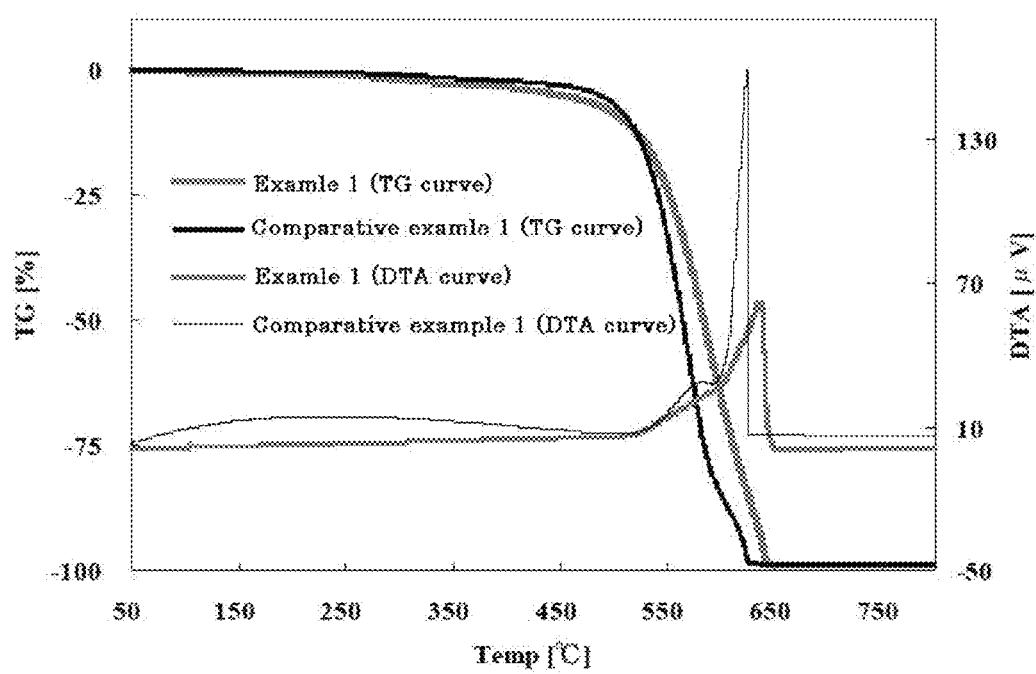

In FIG. 9, the TG/DTA measurement results of the phthalocyanine microparticles of sole Zn—Pc prepared in Example 1 and the phthalocyanine raw material Zn—Pc (Pigment Green 58; manufactured by DIC Corp.) of Example 1, which is Comparative Example 1, are shown. It was confirmed that the decomposition temperature of the microparticle prepared in Example 1 was about 30° C. higher as compared with Comparative Example 1.

In Table 3, the weight-decrease starting temperature P1, the weight decreasing ratio from 40° C. to P1, the weight-decrease ending temperature P2, and the decomposition temperature TR of the phthalocyanine microparticles prepared in Example 1 to Example 5 are shown. Comparative Examples 1 and 5 also shown in Table 3 are data of Zn—Pc and Cu—Pc used as the phthalocyanine raw materials in each of the corresponding Examples. Meanwhile, Zn—Pc and Cu—Pc used as the phthalocyanine raw materials are microparticles (particle diameter of Zn—Pc was about 30 nm and particle diameter of the Cu—Pc was about 100 nm). Comparative Examples 2 to 4 show the data of the phthalocyanine microparticle powder mixtures of sole Zn—Pc and sole Cu—Pc which are prepared in Example 1 and Example 5, respectively, wherein these sole phthalocyanines are mixed so as to give the same mol ratio as each of the corresponding Examples.

TABLE 3

| Example | P1 (° C.) | Weight-decreasing ratio from 40° C. to P1 (% by weight) | P2 (° C.) | TR (° C.) |
|---|---|---|---|---|
| 1 | 391.4 | 2.8 | 634.2 | 537.8 |
| Comparative Example 1 | 407.9 | 7.1 | 581.8 | 507.1 |
| 2 | 397.2 | 2.2 | 650.9 | 534.2 |
| Comparative Example 2 | 387.7 | 3.4 | 587.6 | 492.5 |
| 3 | 392.4 | 2.17 | 662.3 | 545.9 |
| Comparative Example 3 | 374 | 3.3 | 588.9 | 486.2 |
| 4 | 414.2 | 2.31 | 695.5 | 579.1 |
| Comparative Example 4 | 395.1 | 4.2 | 585.3 | 504.5 |
| 5 | 386.2 | 1.84 | 524.0 | 464.4 |
| Comparative Example 5 | 384.6 | 2.68 | 537.6 | 432.6 |

It can be seen that the decomposition temperature is increased in all Examples as compared with Comparative Examples. In addition, it can be seen that, in all Examples, the weight decreasing ratios from 40° C. to the weight-decrease starting temperature P1 in the simultaneous measurements of thermogravimetry and differential thermal are 3% or less by weight and that the weight decreasing ratios of all Examples are smaller than those of Comparative Examples.

From the results shown above, in the present invention, a highly heat resistant phthalocyanine having a higher decomposition temperature than the decomposition temperatures of Zn—Pc and Cu—Pc used as the phthalocyanine raw materials can be provided.

In addition, when a solid solution is made from two or more phthalocyanines, a highly heat resistant phthalocyanine having a higher decomposition temperature than the decomposition temperature of the phthalocyanine microparticle mixtures of sole Zn—Pc and sole Cu—Pc which are separated by mixing a phthalocyanine separating solvent with each of a Zn—Pc solution and a Cu—Pc solution having each of Zn—Pc and Cu—Pc, which are used as phthalocyanine raw materials, dissolved into a solvent can be provided. Further in addition, the obtained highly heat resistant phthalocyanine has the uniform and homogeneous solid solution ratio.

Further, even though the obtained highly heat resistant phthalocyanine is microparticles having particle diameter of 100 nm or less, a highly heat resistant phthalocyanine having a high decomposition temperature can be provided.

EXPLANATION OF REFERENCE NUMERALS 1 first processing surface
2 second processing surface
10 first processing member
11 first holder
20 second processing member
21 second holder
d1 first introduction part
d2 second introduction part
d20 opening

The invention claimed is:
1. A highly heat resistant phthalocyanine, comprising;
a solid solution comprising a copper phthalocyanine and a brominated chlorinated zinc phthalocyanine;
wherein the said phthalocyanine is the phthalocyanine which is separated by mixing a phthalocyanine solution having a phthalocyanine raw material dissolved in a solvent with a phthalocyanine separating solvent, and a decomposition temperature of the separated phthalocyanine is higher by 10° C. or more than a decomposition temperature of the phthalocyanine raw material;
wherein the phthalocyanine is obtained by separating phthalocyanine microparticles by mixing the phthalocyanine solution with the phthalocyanine separating solvent in a thin film fluid formed between at least two processing surfaces which are disposed in a position they are faced with each other so as to be able to approach to and separate from each other, at least one of which rotates relative to the other;
wherein the phthalocyanine solution is a solution having two or more phthalocyanine raw materials dissolved in a solvent, the separated phthalocyanine containing a solid solution of the said two or more phthalocyanine raw materials;
wherein said phthalocyanine raw material is comprised of a copper phthalocyanine and a brominated chlorinated zinc phthalocyanine; and
a decomposition temperature of the separated phthalocyanine is higher by 10° C. or more than a decomposition temperature of a mixture of two or more phthalocyanines that are separated by mixing each of two or more phthalocyanine solutions having the two or more phthalocyanine raw materials dissolved into each solvent with a phthalocyanine separating solvent.

2. The highly heat resistant phthalocyanine according to claim 1, wherein the separated phthalocyanine contains a copper phthalocyanine having its decomposition temperature of 440° C. or higher.

3. The highly heat resistant phthalocyanine according to claim 1, wherein the separated phthalocyanine contains a brominated chlorinated zinc phthalocyanine having its decomposition temperature of 515° C. or higher.

4. The highly heat resistant phthalocyanine according to claim 1, wherein a decomposition temperature of the separated phthalocyanine is 530°C. or higher, and the separated phthalocyanine contains a solid solution of a copper phthalocyanine and a brominated chlorinated zinc phthalocyanine.

5. The highly heat resistant phthalocyanine according to claim 1, wherein its decomposition temperature is calculated from simultaneous measurements of thermogravimetry and differential thermal thereof.

6. The highly heat resistant phthalocyanine according to claim 1, wherein its decomposition temperature is calculated from simultaneous measurements of thermogravimetry and differential thermal thereof, and the measurements thereof are done under an atmospheric condition with the temperature rising rate of 5° C. per one minute while using the reference sample of α-alumina and the sample weight of 10 mg±0.5 mg.

7. The highly heat resistant phthalocyanine according to claim 1, wherein the decomposition temperature thereof is the temperature TR which is the intersection point R between the tangent line L1 at the weight-decrease starting temperature P1 and the tangent line L2 at the weight-decrease ending temperature P2 in the TG curve obtained by simultaneous measurements of thermogravimetry and differential thermal thereof.

8. The highly heat resistant phthalocyanine according to claim 7, wherein its weight decreasing ratio from 40° C. to the weight-decrease starting temperature P1 in simultaneous measurements of thermogravimetry and differential thermal thereof is 3% or less.

9. The highly heat resistant phthalocyanine according to claim 1, wherein the separated phthalocyanine is composed of particles having a particle diameter 100 nm or less.

10. The highly heat resistant phthalocyanine according to claim 1, wherein a solid solution ratio of two or more phthalocyanines in a primary particle of the separated phthalocyanine microparticles relative to a ratio of two or more phthalocyanine raw materials in the phthalocyanine solution mixed with the phthalocyanine separating solvent is within 25% as a degree of precision.

11. The highly heat resistant phthalocyanine according to claim 2, wherein its decomposition temperature is calculated from simultaneous measurements of thermogravimetry and differential thermal thereof.

12. The highly heat resistant phthalocyanine according to claim 3, wherein its decomposition temperature is calculated from simultaneous measurements of thermogravimetry and differential thermal thereof.

13. The highly heat resistant phthalocyanine according to claim 4, wherein its decomposition temperature is calculated from simultaneous measurements of thermogravimetry and differential thermal thereof.

14. The highly heat resistant phthalocyanine according to claim 2, wherein its decomposition temperature is calculated from simultaneous measurements of thermogravimetry and differential thermal thereof, and the measurements thereof are done under an atmospheric condition with the temperature rising rate of 5° C. per one minute while using the reference sample of α-alumina and the sample weight of 10 mg±0.5 mg.

15. The highly heat resistant phthalocyanine according to claim 3, wherein its decomposition temperature is calculated from simultaneous measurements of thermogravimetry and differential thermal thereof, and the measurements thereof are done under an atmospheric condition with the temperature rising rate of 5° C. per one minute while using the reference sample of α-alumina and the sample weight of 10 mg±0.5 mg.

16. The highly heat resistant phthalocyanine according to claim 4, wherein its decomposition temperature is calculated from simultaneous measurements of thermogravimetry and differential thermal thereof, and the measurements thereof are done under an atmospheric condition with the temperature rising rate of 5° C. per one minute while using the reference sample of α-alumina and the sample weight of 10 mg±0.5 mg.

* * * * *